US009629650B2

(12) United States Patent
Hart et al.

(10) Patent No.: US 9,629,650 B2
(45) Date of Patent: *Apr. 25, 2017

(54) SMALL DIAMETER LAPAROSCOPIC TOOL HAVING RELEASABLE TIP

(71) Applicants: University of South Florida, Tampa, FL (US); The Charles Stark Draper Laboratory, Inc., Cambridge, MA (US)

(72) Inventors: Stuart Richard Hart, Tampa, FL (US); Mario Alves Simoes, Pinellas Park, FL (US); Philip James Hipol, Tampa, FL (US); Kevin Hufford, St. Petersburg, FL (US)

(73) Assignees: University of South Florida, Tampa, FL (US); The Charles Stark Draper Laboratory, Inc., Cambridge, MA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/873,963

(22) Filed: Oct. 2, 2015

(65) Prior Publication Data

US 2016/0022304 A1 Jan. 28, 2016

Related U.S. Application Data

(63) Continuation of application No. 14/053,254, filed on Oct. 14, 2013, now Pat. No. 9,186,167, which is a
(Continued)

(51) Int. Cl.
*A61B 17/3205* (2006.01)
*A61B 17/32* (2006.01)
(Continued)

(52) U.S. Cl.
CPC .. *A61B 17/320016* (2013.01); *A61B 1/00087* (2013.01); *A61B 1/00101* (2013.01);
(Continued)

(58) Field of Classification Search
CPC ............ A61B 17/3205; A61B 1/00087; A61B 1/00101; A61B 1/3132; A61B 2017/2931; A61B 1/3135; A61B 1/3137; A61B 1/317
(Continued)

(56) References Cited

U.S. PATENT DOCUMENTS

| 4,174,715 A | 11/1979 | Hasson |
| 5,441,059 A | 8/1995 | Dannan |

(Continued)

FOREIGN PATENT DOCUMENTS

WO 2010114634 A1 10/2010

OTHER PUBLICATIONS

Chow et al., Single Incision Laparoscopic Surgery for Acute Appendicitis Feasibility in Pediatric Patients. Diagnostic and Therapeutic Endoscopy. 2010. Article ID 294958: 1-3.
(Continued)

*Primary Examiner* — Eric Rosen
*Assistant Examiner* — George J Ulsh
(74) *Attorney, Agent, or Firm* — Nilay J. Choksi; Smith & Hopen, P.A.

(57) ABSTRACT

A laparoscopy tool includes a sheath and a control wire slideably disposed within a lumen of the sheath. The sheath has a diameter of less than 1.6 mm and is introduced through an abdominal incision. A handle axially displaces the control wire within the lumen and operates a conventional tip with wire-controlled opposing jaws that is introduced through the umbilicus and has a bore formed in its trailing end. A first set of blades in the bore engage grooves formed in the leading end of the control wire and a second set of blades engages the sheath to prevent sheath retraction. A cam displaces the second set of blades away from the sheath for sheath introduction and removal, and toward the sheath to prevent sheath retraction. The tip is removed through the umbilicus
(Continued)

and the tool is removed through the abdominal incision when the surgery is completed.

10 Claims, 13 Drawing Sheets

Related U.S. Application Data continuation of application No. PCT/US2012/033566, filed on Apr. 13, 2012.

(60) Provisional application No. 61/474,859, filed on Apr. 13, 2011.

(51) Int. Cl.
| | | |
|---|---|---|
| *A61B 1/00* | (2006.01) | |
| *A61B 1/313* | (2006.01) | |
| *A61B 17/34* | (2006.01) | |
| *A61B 17/00* | (2006.01) | |
| *A61B 17/29* | (2006.01) | |

(52) U.S. Cl.
CPC ........ *A61B 1/3132* (2013.01); *A61B 17/3205* (2013.01); *A61B 17/3423* (2013.01); *A61B 17/3421* (2013.01); *A61B 2017/00362* (2013.01); *A61B 2017/2931* (2013.01); *A61B 2017/2946* (2013.01)

(58) Field of Classification Search
USPC ............................................ 606/1, 170, 205
See application file for complete search history.

(56) References Cited

U.S. PATENT DOCUMENTS

| | | |
|---|---|---|
| 5,480,409 A | 1/1996 | Riza |
| 5,893,874 A | 4/1999 | Bourque et al. |
| 7,927,327 B2 | 4/2011 | Lu et al. |
| 2007/0129719 A1 | 6/2007 | Kendale et al. |
| 2008/0064931 A1 | 3/2008 | Schena et al. |
| 2008/0287926 A1 | 11/2008 | Kheir |
| 2008/0319455 A1 | 12/2008 | Harris et al. |
| 2009/0275797 A1 | 11/2009 | Albrecht |
| 2010/0016757 A1 | 1/2010 | Greenburg et al. |
| 2010/0261962 A1 | 10/2010 | Friedberg |
| 2012/0083826 A1 | 4/2012 | Chao et al. |
| 2013/0066304 A1 | 3/2013 | Belson et al. |

OTHER PUBLICATIONS

International Search Report for PCT/US2012/033566 (filing date Apr. 13, 2012) with a mailing date of Oct. 12, 2012; Applicant: University of South Florida et al.

International Preliminary Report on Patentability for PCT/US2012/033566 (filing Apr. 13, 2012) with a priority date of Apr. 13, 2011; Applicant: University of South Florida et al.

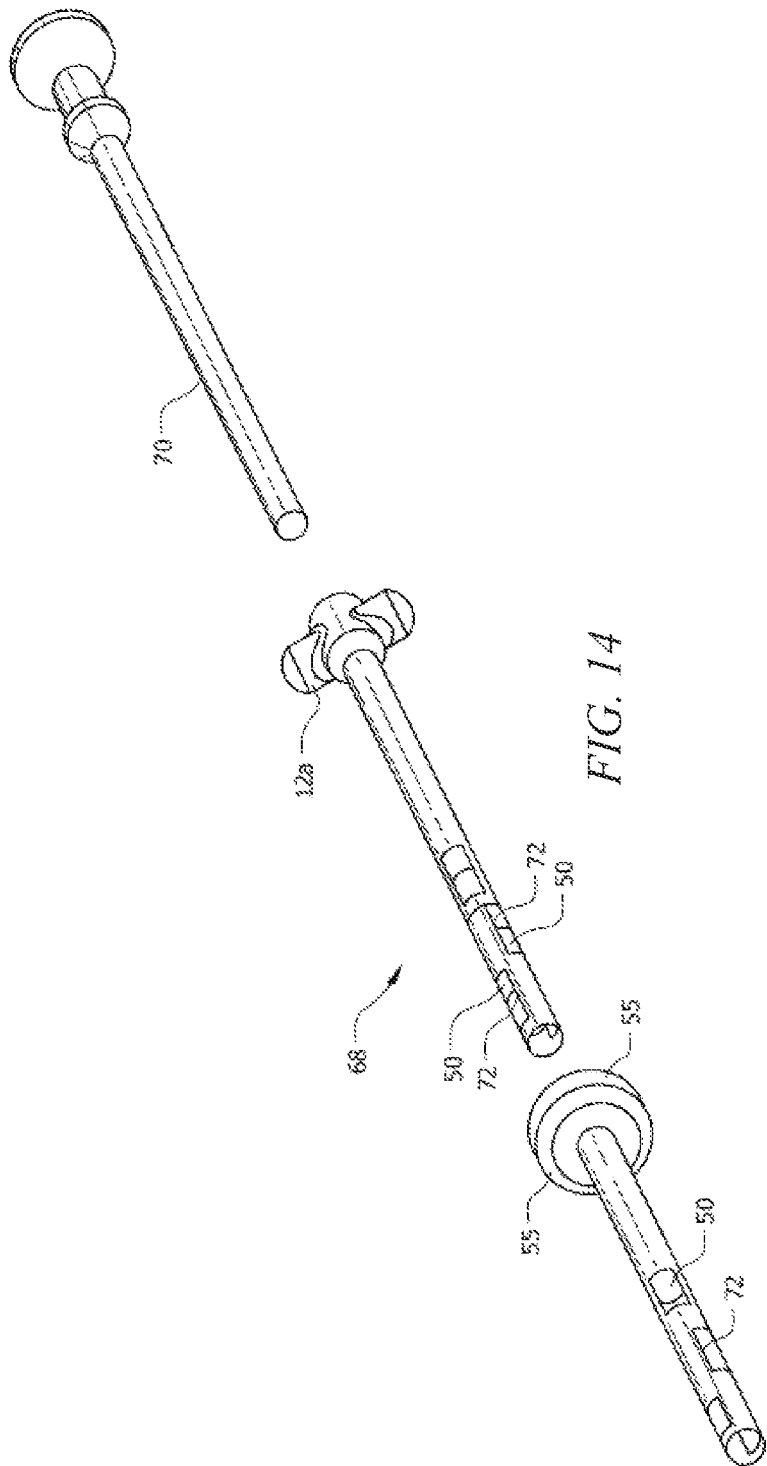

SMALL DIAMETER LAPAROSCOPIC TOOL HAVING RELEASABLE TIP

CROSS-REFERENCE TO RELATED APPLICATIONS

This nonprovisional application is a continuation of and claims priority to U.S. Nonprovisional application Ser. No. 14/053,254, entitled "Small Diameter Laparoscopic Tool Having Releasable Tip", filed Oct. 14, 2013, which is a continuation of and claims priority to PCT Patent Application No. PCT/US2012/033566, entitled "Small Diameter Laparoscopic Tool Having Releasable Tip", filed Apr. 13, 2012, which is a continuation of and claims priority to U.S. Provisional Application No. 61/474,859, entitled "Small Diameter Laparoscopic Tool Having Releasable Tip", filed Apr. 13, 2011, all of which are incorporated by reference in their entireties.

BACKGROUND OF THE INVENTION

1. Field of the Invention

This invention relates, generally, to surgical tools. More particularly, it relates to small diameter laparoscopic surgical tools.

2. Brief Description of the Prior Art

FIG. 1 depicts conventional laparoscopic surgery tool 10 having stationary handle 12 connected to sheath 14. Control rod or wire 16 is slideably disposed within a lumen of sheath 14 and its proximal end is connected to actuating handle 18 that is pivotally connected to stationary handle 12. Control rod or wire 16 is pushed or pulled within the lumen so that it extends or retracts relative to a distal free end of sheath 14 in response to manipulation of handle 18 by a surgeon.

Tip mechanism 20 is connected to the distal free end of sheath 14 as best depicted in FIG. 2. Tip 20 includes pivotally mounted opposed jaws 20a, 20b that are depicted in their open configuration in FIG. 2 and in their closed configuration in FIG. 1. Jaws 20a, 20b are opened and closed by the extension and retraction, respectively, of control rod or wire 16 to enable tasks such as pinching, cutting, clamping, spreading, suturing, and the like.

Tools such as tool 10 typically have a sheath diameter of five millimeters (5 mm) or more. Conventional laparoscopic surgical technology therefore requires an incision in a patient's abdominal wall that can leave a scar and contribute to post-operative pain. Scarring is avoided only if an incision has a length of 1.6 mm or less.

An alternative methodology that avoids scarring and that reduces post-operative pain includes insertion of laparoscopic tools through a single port in the patient's umbilicus. Such undepicted procedures are difficult because the tools must be used in close proximity to one another. In FIG. 3, three (3) laparoscopy tools denoted 22, 23, and 24 are depicted in a triangulation array that is not possible when all of such tools are inserted through the umbilicus.

Smaller-in-diameter laparoscopic tools, one of which is depicted in FIG. 4 and denoted by the reference numeral 10a, have recently been introduced in an effort to reduce the likelihood of scarring. These tools enable tip 20a to be retracted within the lumen of sheath 14. However, the small size of tip 20a limits its utility, i.e., it is not robust because it has limited surface area or limited force capability for many common surgical procedures. Moreover, the smallest diameter tool, having a sheath diameter of 2.5 mm, is still too large to reduce the likelihood of scarring.

Thus there is a need for a robust laparoscopic tool that can perform pinching, cutting, clamping, spreading, suturing, and other such surgical procedures while requiring an abdominal wall incision that does not exceed 1.6 mm so that such tool can be used in a triangulation array of tools.

However, in view of the art considered as a whole at the time the present invention was made, it was not obvious to those of ordinary skill in the art how such a small tool could be provided with the required robust structure.

BRIEF SUMMARY OF THE INVENTION

The long-standing but heretofore unfulfilled need for a laparoscopy tool having a robust tip of conventional size that can be used with an incision that does not exceed 1.6 mm is now met by a new, useful, and non-obvious invention.

The novel laparoscopy tool includes a sheath having a diameter of 1.6 mm or less. A control rod or wire is slideably disposed within the lumen of the small diameter sheath in concentric relation thereto, i.e., the control rod or wire is coincident with the longitudinal axis of symmetry of the small diameter sheath.

A handle has a fixed position part to which the small diameter sheath is mounted and a movable part engaged to a proximal end of the control rod or wire, hereinafter referred to as a control wire, for axially displacing the control wire within the lumen of the small diameter sheath in either axial direction, i.e., proximal-to-distal to open the jaws and distal-to-proximal to close the jaws.

A tip of conventional size has opposed jaws that open and close as the control wire is displaced within the lumen. However, the tip of conventional size is introduced through the umbilicus by means of a conventional laparoscope tool having a large diameter sheath. The novel control wire and small diameter sheath are introduced through an abdominal incision that is less than 1.6 mm in length. A novel docking mechanism is added to the trailing end of the conventional tip so that the novel control wire and small diameter sheath can be releasably connected to the conventional tip after the robust tip has been introduced through the umbilicus.

The trailing end of a conventional tip includes a truncate tube having a hollow bore or lumen. The hollow bore is modified by the addition of a novel docking mechanism that enables the robust tip to be engaged and released by the novel small diameter sheath after the robust tip has been introduced into a patient's body through the umbilicus.

The novel docking mechanism includes a first and a second blade having a common length. Each blade is flat and formed of a flexible and resilient material. The blades are mounted within the bore in diametrically opposed relation to one another and in transverse relation to a longitudinal axis of the bore. When in repose, the blades extend radially inwardly towards a longitudinal axis of symmetry of the bore. Their radially innermost ends are spaced apart from one another by a space having less breadth than the breadth of the control wire.

A first groove is formed in a leading end of the control wire on a first side thereof and a second groove is formed in the leading end of the control wire on a second, opposite side thereof. The first and second grooves are transversely disposed relative to a longitudinal axis of the control wire and the first and second grooves respectively receive the first and second blades when the control wire is inserted into the bore.

The leading end of the control wire is beveled to facilitate transient displacement of the radially innermost ends of the first and second blades when the control wire is advanced in a proximal-to-distal direction by actuation of the conventional handle. The first and second transversely disposed blades snap into the first and second transversely disposed grooves, respectively, under their inherent bias after the momentary displacement, thereby returning to their position of repose. The control wire is generally flat so that it disengages from the blades when rotated ninety degrees (90°) about its longitudinal axis.

A third and a fourth blade, also sharing a common length and being formed of a flat, flexible and resilient material, are mounted within the same bore in proximal, longitudinally spaced relation to the first and second blades, in diametrically opposed relation to one another, and in transverse relation to the longitudinal axis of the bore, i.e., in parallel relation to the first and second blades. When in repose, the third and fourth blades extend radially inwardly towards a longitudinal axis of symmetry of the bore. The radially innermost ends of the third and fourth blades are spaced apart from one another by a space having less breadth than the breadth of the small diameter sheath.

The radially innermost ends of the third and fourth blades, when in repose, engage the exterior wall of the small diameter sheath and prevent retraction of the small diameter sheath in a distal-to-proximal direction. The third and fourth blades are disposed in the bore in longitudinally spaced apart, proximal relation to the first and second blades as aforesaid so that a leading end of the control wire extends past the third and fourth blades before the small diameter sheath is engaged by the third and fourth blades.

A cam is rotatably mounted in a proximal end of the bore and is centrally apertured to enable the control wire and the small diameter sheath to extend therethrough. The cam is positioned in close proximity to the third and fourth blades, on the proximal side thereof and is introduced and withdrawn through the incision in the umbilicus because it is a part of the robust tip. A flat is formed in the central aperture of the cam and said flat mates with a flat formed in the small diameter sheath so that rotation of the small diameter sheath about its longitudinal axis of symmetry causes conjoint rotation of the cam. The other parts of the robust tip do not rotate when the cam rotates.

The sheath and inner wire are inserted into the bore formed in the proximal end of the robust tip, and then rotated ninety degrees (90°) to lock them into place. The rotation causes the rotatably mounted cam to rotate, which releases pressure on the blades at the proximal end to contact and lock the sheath in place. The rotation also causes the inner wire to engage with the blades on the distal end, locking the wire into place. An indentation on the cam keeps the cam from rotating backwards and releasing the blades.

The cam has rises formed therein that displace the third and fourth blades in a proximal-to-distal direction when the cam is rotated in a first direction, creating a clearance space between radially innermost ends of the third and fourth blades and the small diameter sheath so that the small diameter sheath may be introduced into the bore formed in the trailing end of the conventional tip. The cam is locked into place by indentations formed in the blades. After the small diameter sheath has been inserted, the cam is released from the indentations and rotated in a second direction opposite to the first direction so that the blades slide down the rises into engagement with the small diameter sheath, thereby preventing retraction of the small diameter sheath in a distal-to-proximal direction. The cam is rotated by rotation of the small diameter sheath.

The tool holder that is introduced through the umbilicus holds the conventional laparoscopic tool having the rotatably mounted cam formed in the bore. The cam is free to rotate, and follows the flat side of the sheath.

The control wire and small diameter sheath are both non-round, preferably hexagonal, in transverse section so that the small diameter sheath and control wire rotate conjointly with one another about their common longitudinal axis of symmetry. The leading or distal end of the control wire, however, is flat so that it disengages from the first and second blades when rotated as aforesaid.

Accordingly, a robust, relatively large conventional tip is introduced through a patient's umbilicus, independently of the novel tool. The novel tool, with no tip, is then introduced through an incision, no greater than 1.6 mm, in the abdominal wall. The distal or leading end of the novel tool is then engaged to the tip by advancing the control wire into engagement with the first and second blades and the small diameter sheath into engagement with the third and fourth blades.

The robust tip is then used as needed in a conventional way. When the surgery is completed, the small diameter sheath and hence the control wire are rotated ninety degrees (90°) and such rotation disengages the control wire from the first and second blades and the small diameter sheath from the third and fourth blades through the action of the cam. This disengages the novel tool from the robust tip so that the novel tool can be withdrawn through the 1.6 mm or less incision and the conventional, robust tip, including the cam and the blades, is withdrawn through the umbilicus using the conventional laparoscope.

The robust tip is housed prior to deployment within a tip dispenser which is a truncate tube that is hingedly mounted to the large diameter sheath of a conventional laparoscope near the distal end of said large diameter sheath. The large diameter sheath has a cut-out formed in it that matches the length and diameter of the tip dispenser so that the outer wall of the tip dispenser is flush with the outer wall of the laparoscope large diameter sheath when the tip dispenser is in an undeployed configuration. This enables the large diameter sheath and the novel tip dispenser to be inserted through a twelve millimeter (12 mm) incision in the umbilicus in accordance with conventional practice.

A deployment mechanism is then operated by the user to cause the tip dispenser to pivot about a hinge so that the longitudinal axis of the tip dispenser is disposed at a predetermined oblique angle relative to the longitudinal axis of the large diameter sheath. The trailing end of the robust tip is engaged by the leading end of the small diameter sheath and withdrawn from the tip dispenser.

In an alternative embodiment, a second sheath that ensleeves the large diameter sheath has at least one opening formed therein. Each tip dispenser is biased to deploy outwardly but the bias cannot unload unless the at least one opening is in registration with the tip dispenser. The at least one opening is sized to accommodate a tip dispenser therethrough so that alignment of the at least one opening and a tip dispenser results in unloading of the bias means and deployment of the tip dispenser.

The robust tip is operated by the surgeon to perform surgical procedures. The jaws of the robust tip are then closed and the robust tip is returned to the tip dispenser. The small diameter sheath is rotated ninety degrees (90°) to disengage the robust tip from the small diameter sheath. The said small diameter sheath is withdrawn through the small incision in the abdominal wall and the robust tip and its housing are withdrawn through the umbilicus.

The primary object of this invention is to enable the use of a robust tip during laparoscopic surgery while making an incision in an abdominal wall that does not exceed 1.6 mm in length.

A closely related object is to provide a small diameter laparoscopy tool and a conventional, relatively large-sized, robust tip that may be releasably engaged to one another in order to accomplish the foregoing object.

These and other important objects, advantages, and features of the invention will become clear as this description proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 14 is an exploded perspective view of the parts depicted in FIG. 13.

DETAILED DESCRIPTION OF THE PREFERRED EMBODIMENT

Figure 1:
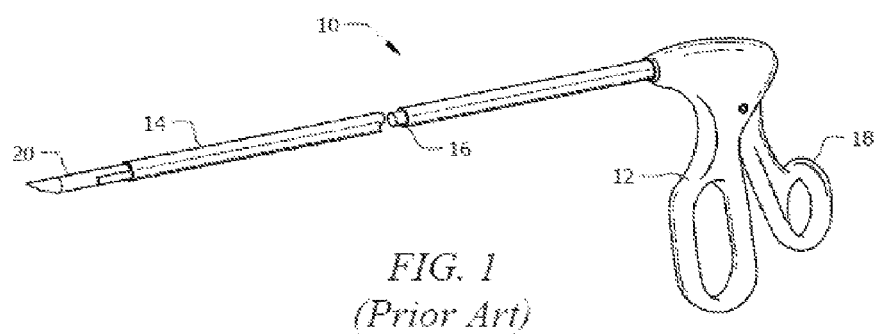
FIG. 1 is a perspective view of a prior art laparoscopic surgery tool.
Figure 2:
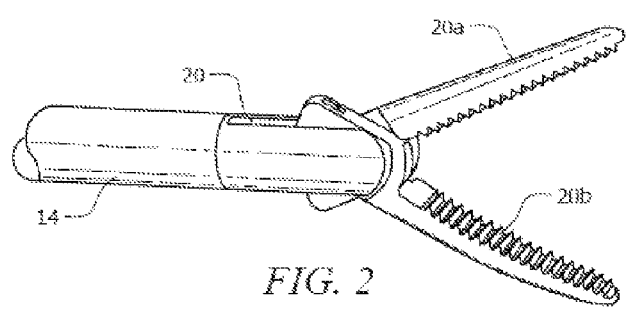
FIG. 2 is a perspective view of a prior art tip at the distal free end of a large diameter sheath of a prior art laparoscopic surgery tool.
Figure 3:
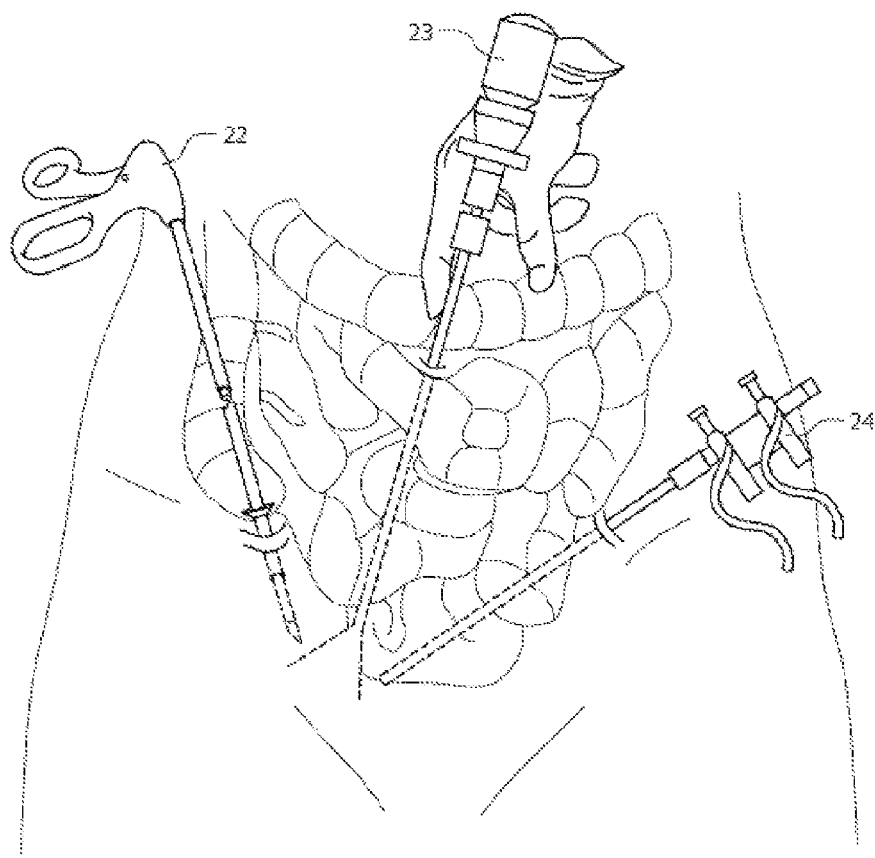
FIG. 3 is a perspective view depicting prior art triangulation of three (3) prior art laparoscopic tools during pelvic laparoscopic surgery.
Figure 4:
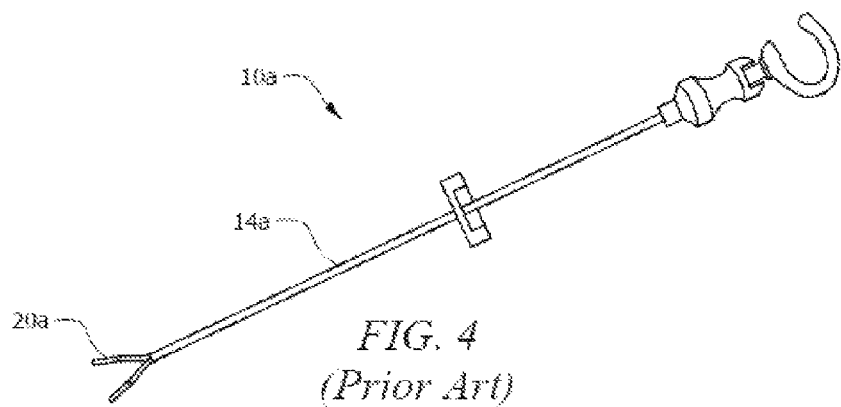
FIG. 4 is a side elevational view of a prior art retractable tip laparoscopic surgery tool.

Prior art tools are depicted in FIGS. 1-4 as above-disclosed and embodiments of the novel instrument are depicted in FIGS. 5-14.

The novel apparatus enables a surgeon to use a variety of standard size laparoscopic tips without compromising tip size or force capability, while greatly minimizing the likelihood of scarring of a patient.

Novel laparoscopic surgery tool 30 includes a small diameter (1.6 mm or smaller) sheath 32 having a lumen that slideably receives control rod or wire 34 therewithin, hereinafter referred to as control wire 34. Tool 30 contemplates sheath 32 having a diameter up to 2.5 mm as well since full-size laparoscopic tool tips can still be utilized, though a diameter of 1.6 mm or smaller is preferred. Small diameter sheath 32 is inserted into the body through a small incision in the abdominal wall (1.6 mm or smaller) and docked or connected to a conventional size (5 mm or greater) laparoscopic surgery tip 20 within the abdominal cavity. The large, robust tip 20 is introduced into the body through a larger opening in the patient's umbilicus. A conventional laparoscope having a sheath that is about twelve millimeters (12 mm) in diameter is used for such purpose. Following use, robust conventional tip 20 is undocked or disconnected from small diameter sheath 32 and removed from the patient through the umbilicus using the conventional sheath. Small diameter sheath 32 and control wire 34 are removed from the body through the small (1.6 mm or smaller) incision in the patient's abdominal wall.

Figure 5:
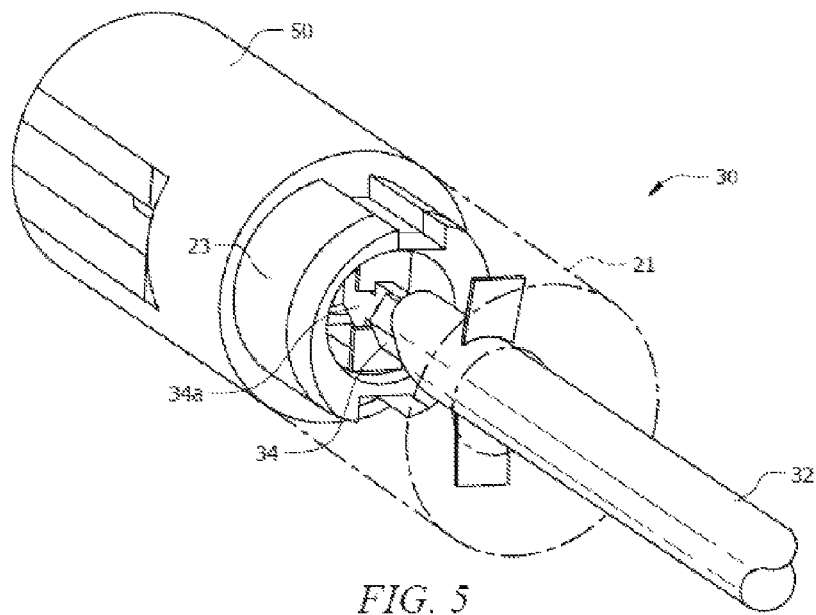
FIG. 5 is a perspective view of the novel apparatus for releasably interlocking a small diameter laparoscopy tool to a robust tip.
Figure 6A:
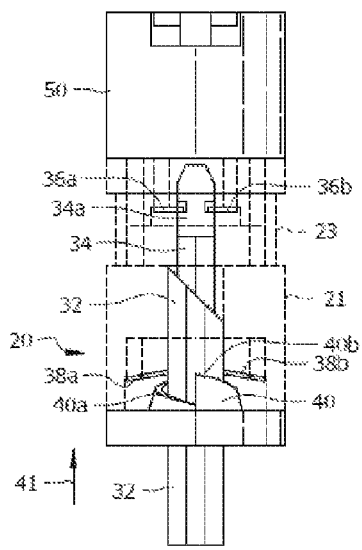
FIG. 6A is an elevational view of the novel docking apparatus when the small diameter tool is connected to the relatively large diameter tip.
Figure 6B:
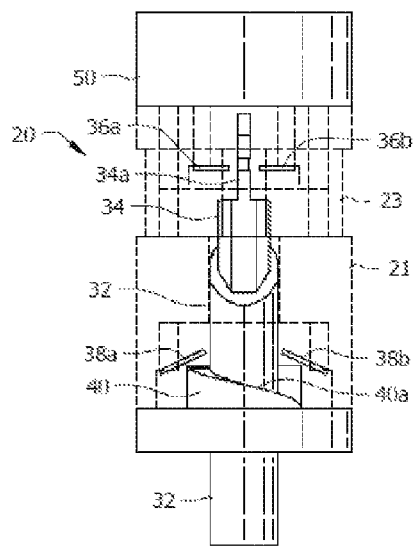
FIG. 6B is an elevational view of the novel docking apparatus when the small diameter tool is rotated about its longitudinal axis of symmetry by ninety degrees (90°) and thus disconnected from the relatively large diameter tip.

Small diameter sheath 32 and control wire 34 are formed or machined in a non-round, preferably hexagonal shape as depicted in FIGS. 5, 6A and 6B. This enables conjoint rotation of novel laparoscopic tool 30, small diameter sheath 32, and control wire 34. As will become clear as this disclosure proceeds, a ninety degree (90°) rotation of small diameter sheath 32 and control wire 34 relative to tip 20 disengages said small diameter sheath 32 and control wire 34 from tip 20. Small diameter sheath 32 and control wire 34 are then removed from the small (1.6 mm or smaller) incision and robust tip 20 is removed through the larger incision in the umbilicus with a conventional laparoscope as aforesaid.

Novel tool 30 facilitates procedures involving larger diameter laparoscopic shafts because it reduces the likelihood of scarring by eliminating the need to introduce relatively large tools through large incisions in the abdominal wall. Tool 30 also allows a surgeon to use standard size, conventional robust tips having greater force capability and larger surface area than smaller laparoscopic tools with retractable tips.

Docking and undocking of robust laparoscopic tool tip 20 with tool 30 requires the capture and release of small diameter sheath 32 within the stationary, proximal part (trailing end) of tip 20 and control wire 34 within the distal, movable part (leading end) of tip 20. A bore is formed in the proximal, trailing end of tip 20 and two (2) sets of blades and a cam are positioned within said bore to enable facile engagement and disengagement of laparoscopy tool 30 to the tip. The two sets of blades are a leading or distal set of blades that engage control wire 34 and a trailing or proximal set of blades that engage small diameter sheath 32.

More particularly, as depicted in FIGS. 5, 6A and 6B, a first pair of blades, denoted 36a, 36b, is mounted in said bore at the distal end thereof. Each blade has a radial extent less than the diameter of control wire 34 so that the radially innermost end of each blade is momentarily displaced in a proximal-to-distal direction when control wire 34 is inserted into the bore formed in the proximal end of tip 20. After said bending, both blades snap into place under their inherent bias and are captured by grooves formed in opposing sides of control wire 34, there being one groove to accommodate the radially innermost end of each blade. The grooves are clearly visible in said FIGS. but are unnumbered to avoid cluttering of the drawings.

This locking mechanism engages control wire 34 to tip 20 so that axial displacement of control wire 34 actuates the moving, distal end of tip 20, i.e., axial displacement of control wire 34 in a proximal-to-distal direction opens jaws 20a, 20b of tip 20 and axial displacement of control wire 34 in a distal-to-proximal-direction closes said jaws. An elastomeric material is positioned between the end of control wire 34 and the movable part of tip 20 to maintain intimate contact between blades 36a, 36b and control wire 34 as control wire 34 is displaced in the axial direction.

A second set of blades, denoted 38a, 38b, each of which has a radial extent less than the diameter of small diameter sheath 32, is mounted in the bore formed in the proximal end of tip 20 in diametrically opposed relation to one another. Prior to insertion of small diameter sheath 32 into the bore formed in the proximal end of tip 20, the radially innermost ends of blades 38a, 38b are displaced in a proximal-to-distal direction by rises 40a formed in cam 40, as indicated in FIG. 6A by directional arrow 41, when cam 40 is rotated in a first direction. When blades 38a, 38b have been fully displaced, said blades engage indentations 40b formed in rises 40a and are held in the open position. Small diameter sheath 32 is then inserted into the bore.

After small diameter sheath 32 is inserted into the bore, cam 40 is rotated in a second direction opposite to said first direction. Blades 38a, 38b are thus disengaged from indentations 40b and therefore slide down rises 40a into engagement with the exterior surface of small diameter sheath 32. This prevents retraction of small diameter sheath 32 in a distal-to-proximal direction. Friction forces developed between blades 38a, 38b and small diameter sheath 32 holds small diameter sheath 32 to the proximal, stationary part of tip 20. Movement of small diameter sheath 32 in the direction of separation (distal-to-proximal) causes blades 38a, 38b to clamp or self-lock against small diameter sheath 32, increasing the friction force, thereby preventing small diameter sheath 32 from being removed from tip 20.

The disengagement of tip 20 from small diameter sheath 32 is depicted in FIG. 6B. Ninety degree (90°) rotation of small diameter sheath 32 from its FIG. 6A position to its FIG. 6B position causes cam 40 to displace blades 38a, 38b in a further proximal-to-distal displacement, thereby lifting and thus disengaging the blades from small diameter sheath 32 so that said sheath can be retracted. FIG. 6B should be interpreted as including a clearance space between blades 38a, 38b and small diameter sheath 32. When blades 38a, 38b are fully disengaged from small diameter sheath 32, they are locked into place by said indentations 40b formed in cam 40 so that small diameter sheath 32 can be withdrawn.

The same rotation rotates control wire 34 so that the grooves formed in the flat leading end thereof disengage from blades 36a, 36b as is ascertainable from a comparison of FIGS. 6A and 6B. As mentioned above, small diameter sheath 32 and control wire 34 are non-round so that said parts rotate conjointly when a surgeon rotates the conventional handle of tool 30. Small diameter sheath 32 and control wire 34 are preferably hexagonal in transverse section except for the flat leading end of control wire 34. After the rotation, i.e., when they are in the FIG. 6B position, they are retracted through the 1.6 mm diameter or smaller incision in the abdominal wall, leaving tip 20 in the patient for subsequent removal through the larger incision made in the umbilicus.

Figure 7A:
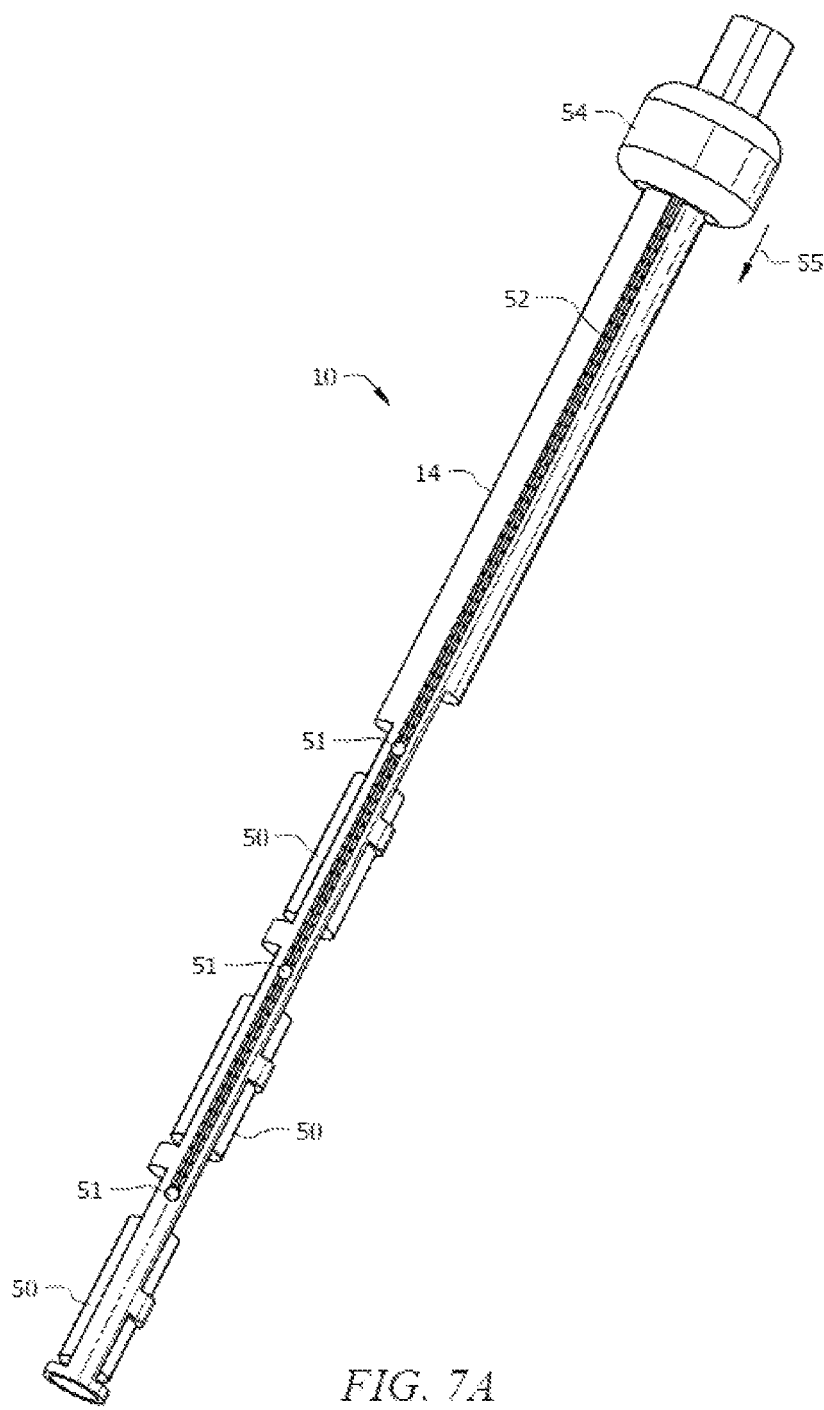
FIG. 7A is a perspective view of the large diameter sheath that carries a plurality of tip dispensers when the tip dispensers are undeployed.
Figure 7B:
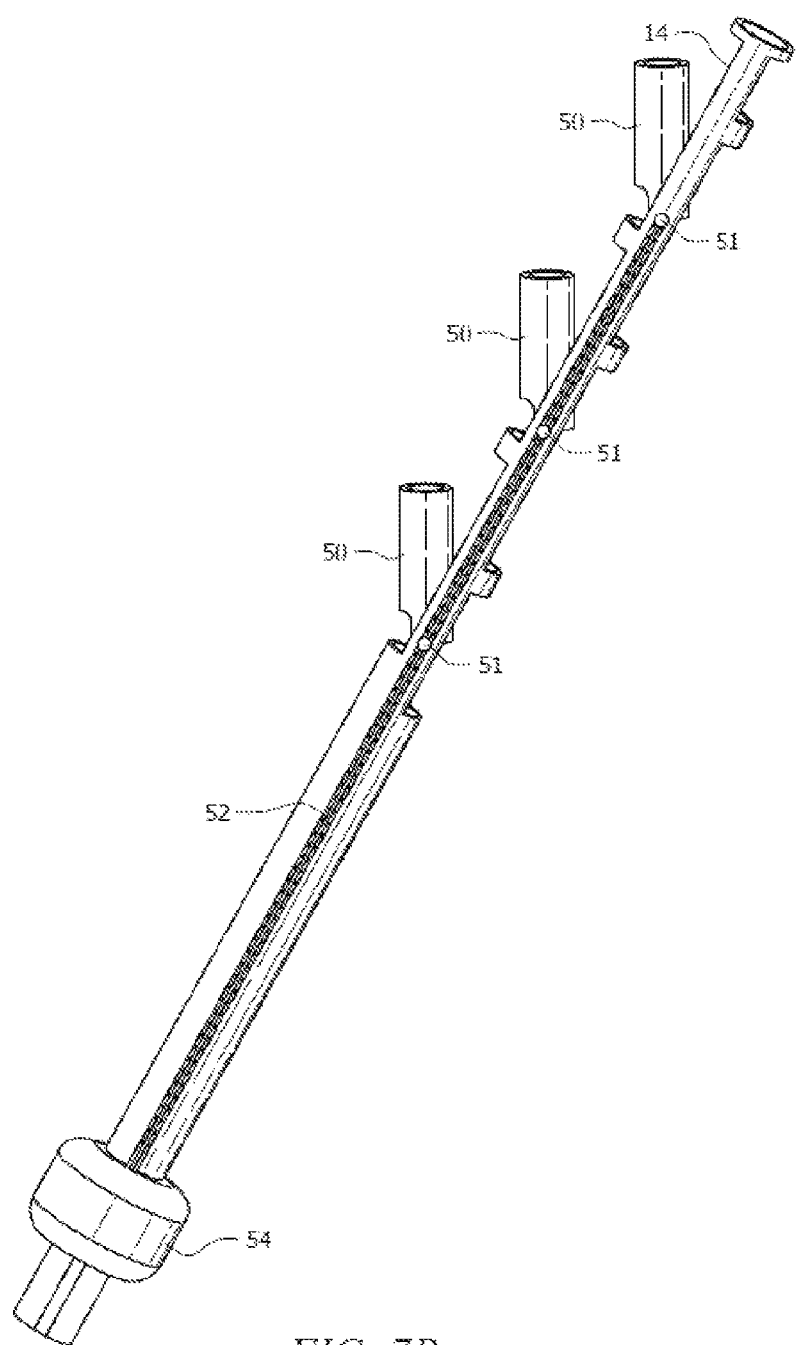
FIG. 7B is a perspective view of the large diameter sheath that carries a plurality of tip dispensers when the tip dispensers are deployed.
Figure 7C:
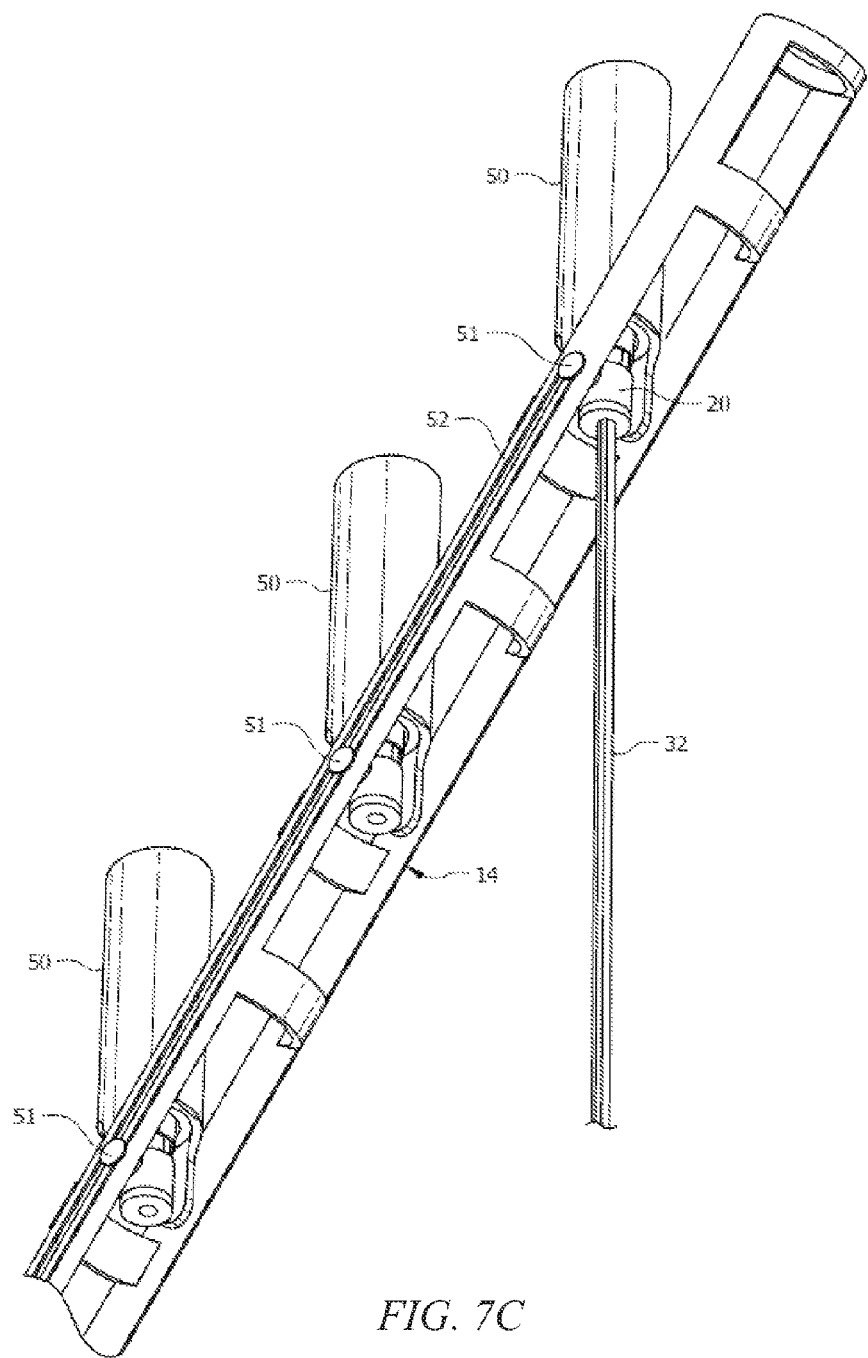
FIG. 7C is a perspective view of the large diameter sheath that carries a plurality of tip dispensers when the tip dispensers are deployed and when a robust tip is disposed within each of the tip dispensers and one of the robust tips is engaged at its trailing end by the small diameter sheath.

Referring now to FIGS. 7A-C, robust tip 20 is housed prior to deployment within tip dispenser 50 which is a truncate tube that is hingedly mounted to large diameter sheath 14 of conventional laparoscope 10 near the distal end of said large diameter sheath. Large diameter sheath 14 has a cut-out formed in it that matches the length and diameter of tip dispenser 50 so that the outer wall of tip dispenser 50 is flush with the outer wall of large diameter sheath 14 when tip dispenser 50 is in an undeployed configuration as depicted in FIG. 7A. This enables large diameter sheath 14 and novel tip dispenser 50 to be inserted through a twelve millimeter (12 mm) incision in the umbilicus in accordance with conventional practice.

A deployment mechanism, disclosed in connection with FIGS. 8 and 9 hereinafter, is then operated by the user to cause each tip dispenser 50 to pivot about its hinge 51 so that the longitudinal axis of each tip dispenser 50 is disposed at a predetermined oblique angle relative to the longitudinal axis of large diameter sheath 14 as depicted in FIG. 7B-C.

Robust tip 20 is then engaged by the leading end of small diameter sheath 32 as depicted in FIG. 7C and retracted from truncate tube/tip dispenser 50 so that tip 20 fully exits said truncate tube. The jaws of robust tip 20 are closed when said tip 20 is housed within tip dispenser 50. The tubular trailing end of robust tip 20, including the first, second, third and fourth blades, and the cam, is engaged by the small (1.6 mm) diameter sheath 32 having said concentric control wire 34 in its lumen in the manner disclosed above.

The depicted embodiment includes three (3) tip dispensers 50 in the form of truncate tubes but the scope of this invention includes one or more of said tip dispensers.

Tip dispensers 50 are preferably deployed by retracting knob 54 in a distal-to-proximal direction and said tip dispensers are returned to their undeployed, FIG. 7A positions by displacing said knob 54 in a proximal-to-distal direction. However, those of ordinary skill in the mechanical arts can create mechanisms that operate in the opposite way and such mechanisms are within the scope of this invention Mechanisms that deploy and retract tip dispensers 50 by rotating knob 54 about the longitudinal axis of large diameter sheath 14 are also within the scope of this invention.

Figure 8:
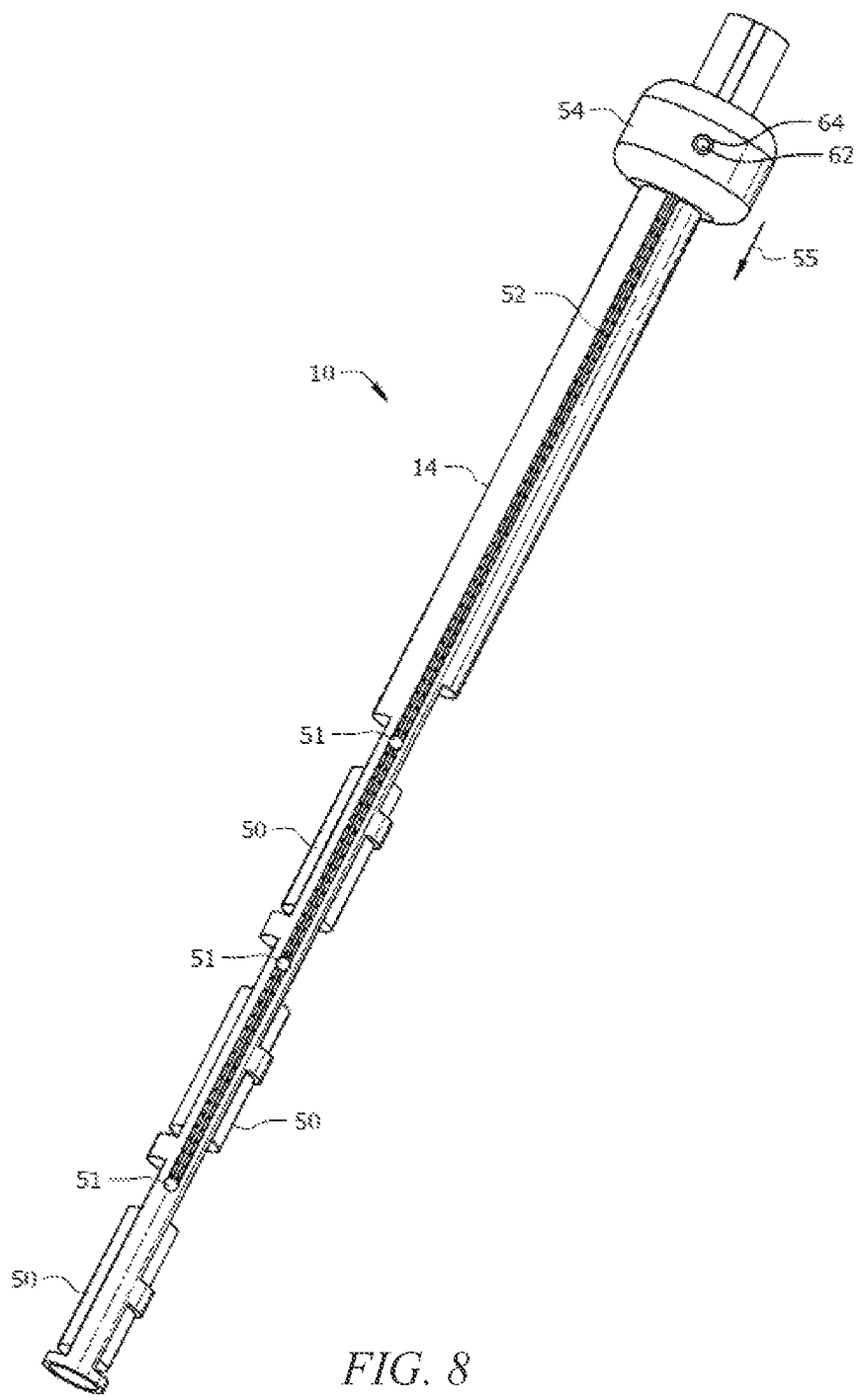
FIG. 8 is a perspective view depicting the tip dispenser deployment mechanism.
Figure 9:
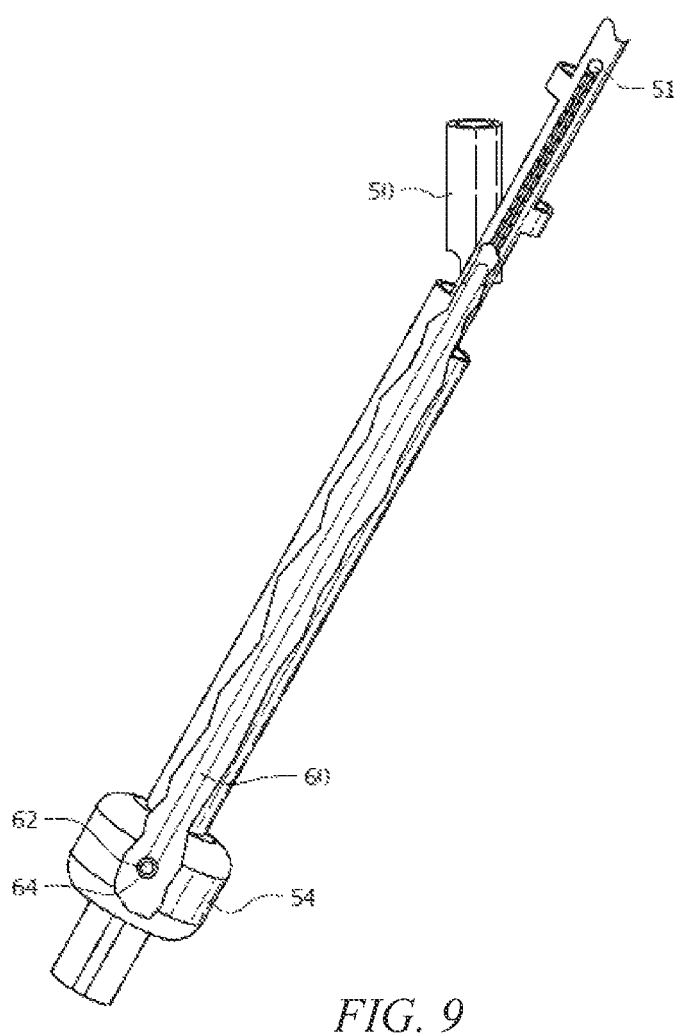
FIG. 9 is a partially cut-away perspective view depicting the tip dispenser deployment mechanism.

One way to effect deployment and retraction of tip dispensers 50 is depicted in FIGS. 8 and 9. Elongate rigid rod 60 (FIG. 9) is connected to knob or handle 54 so that proximal-to-distal displacement of knob 54 as indicated by directional arrow 55 in FIG. 8 causes housings 50 to pivot outwardly (FIG. 9) into their respective deployed positions and distal-to-proximal displacement of said knob returns the housings to their respective undeployed, FIG. 8 positions.

More particularly, opening 64 (FIGS. 8 and 9) is formed in knob 54 and button or protuberance 62, formed in rod 60 near its proximal end, extends through said opening so that said button prevents rotation of rod 60 and so that proximal-to-distal and distal-to-proximal travel of knob 54 is transmitted directly to said rod.

Elongate rod 60 is disposed within large diameter sheath 14 in parallel relation to a longitudinal axis of said large diameter sheath and knob 54 is slideably mounted to a proximal end of said large diameter sheath. The proximal end of elongate rod 60 is secured to knob 54 as aforesaid so that axial displacement of knob 54 relative to large diameter sheath 14 causes conjoint axial displacement of elongate rod 60.

Elongate rod 60 is hingedly connected to each tip dispenser 50 so that proximal-to-distal displacement of knob 54 causes each tip dispenser 50 to pivot into a deployed position at a predetermined oblique angle relative to the longitudinal axis of large diameter sheath 14 and so that distal-to-proximal displacement of knob 54 causes each tip dispenser 50 to return to its undeployed position. The position of rod 60 is such that it does not interfere with engagement of the trailing end of each robust tip 20 by small diameter sheath 34 and the removal of each robust tip from its dispenser 50.

Figure 10:
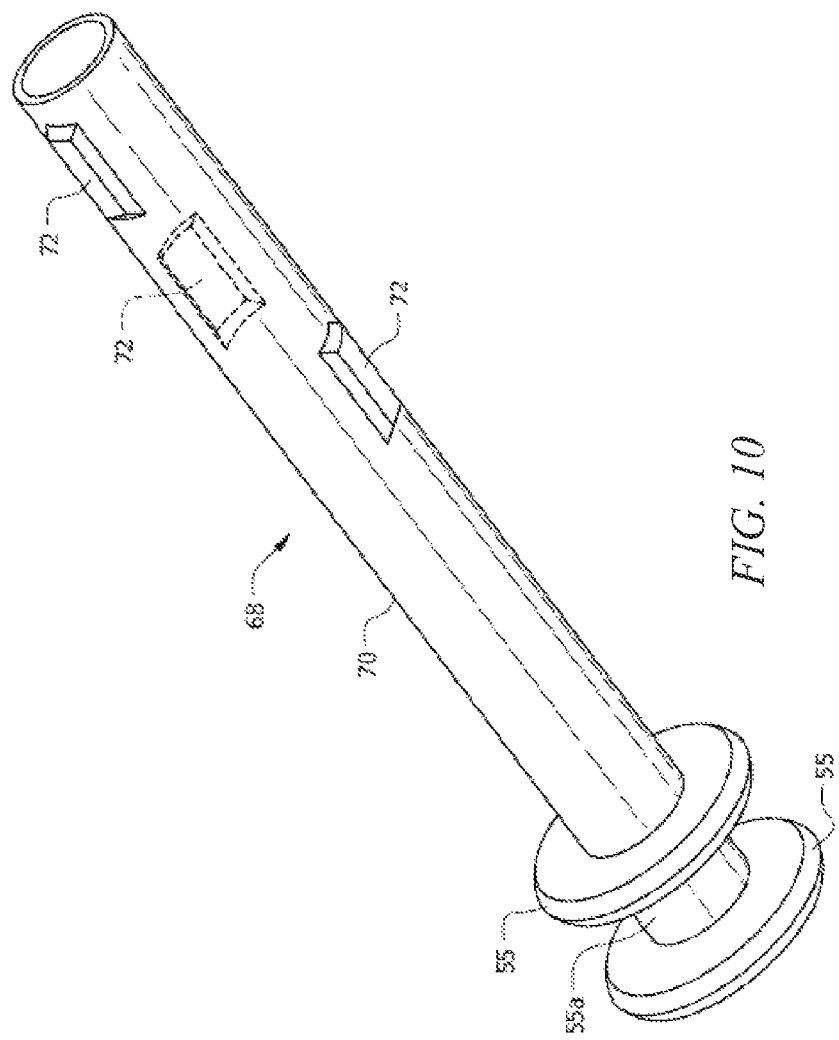
FIG. 10 is a perspective view of a second sheath of an alternative embodiment that ensleeves the large diameter sheath of the first embodiment.

An alternative way to effect deployment and retraction of each tip dispenser 50 is to position a bias means such as a spring in large diameter sheath 14 that urges its associated tip dispenser 50 into its deployed position. Deployment is controlled by the use of second sheath 68 as depicted in FIG. 10 that includes tube 70 having openings 72 formed therein and which ensleeves large diameter sheath 14.

Figure 11:
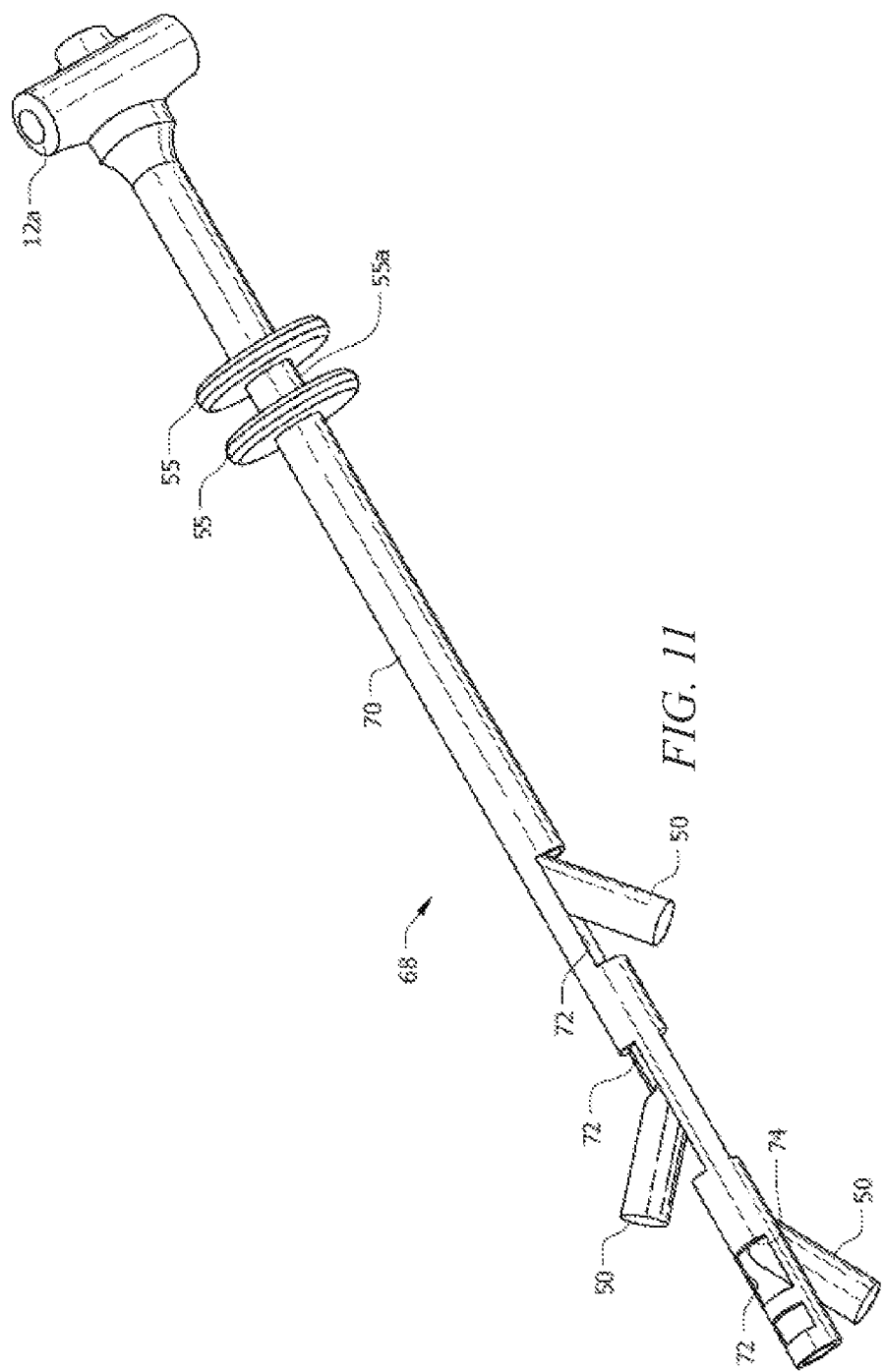
FIG. 11 is a perspective view depicting the alternative embodiment with tip dispensers in their respective deployed positions.

Each opening 72 slightly exceeds the width and length of the tip dispensers 50 so that said tip dispensers can extend therethrough when in their angled, deployed positions as depicted in FIG. 11. Openings 72 line up with each tip dispenser when second sheath 68 is rotated or axially displaced, or both, relative to large diameter sheath 14 as required to bring said openings into registration with their associated tip dispensers, thereby allowing the bias means to unload and thus to deploy each tip dispenser into its oblique, deployed position through its associated opening 72.

Figure 12:
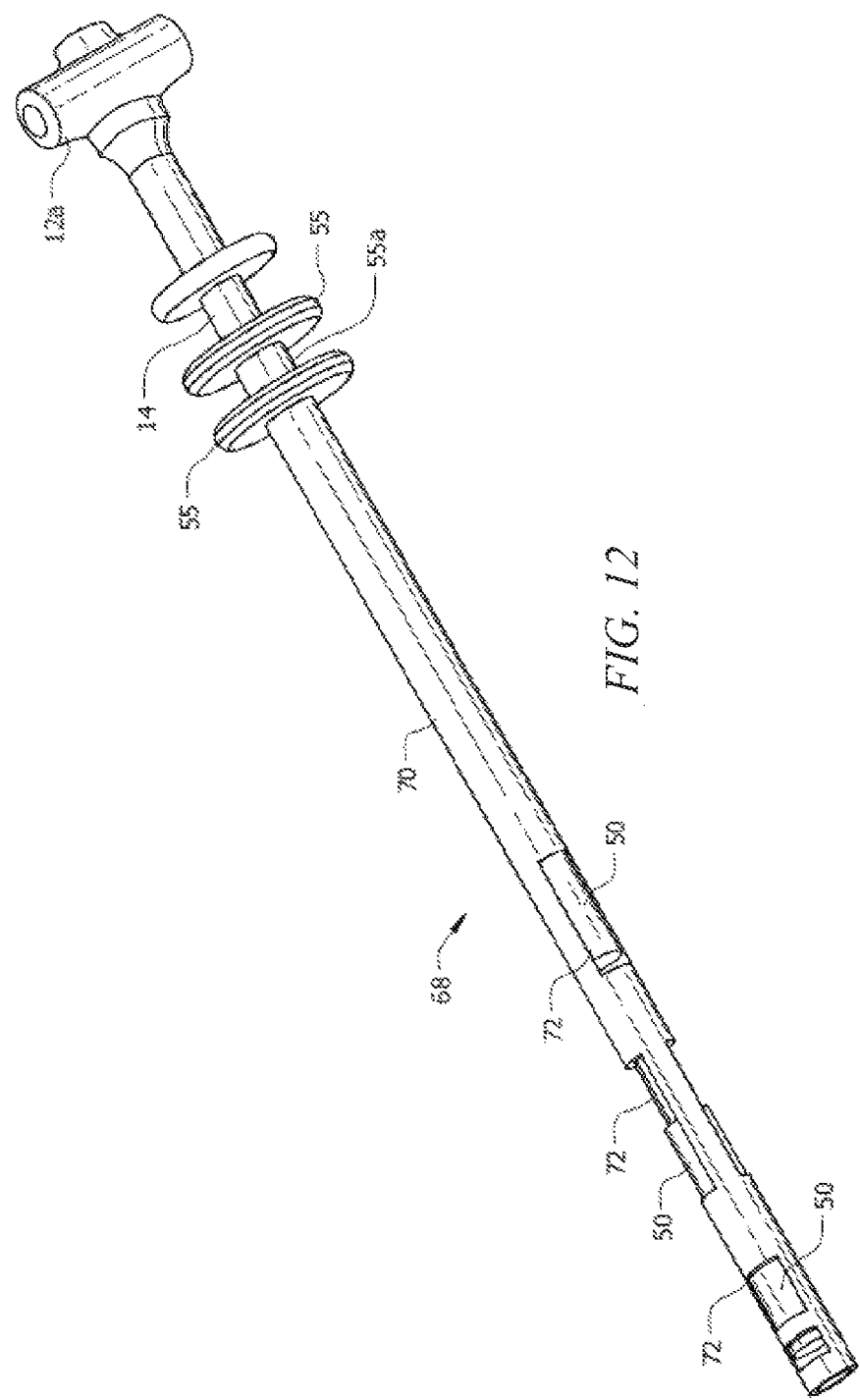
FIG. 12 is a perspective view depicting the alternative embodiment with the tip dispensers in their respective undeployed positions.

Second sheath 68 is further rotated or axially displaced, or both, relative to large diameter sheath 14 as required to displace openings 72 out of registration with their associated tip dispensers 50, thereby pushing the tip dispensers back into their respective unrotated, undeployed positions as depicted in FIG. 12, thereby loading the bias means. The novel assembly 68 is withdrawn in its FIG. 12 configuration through the incision in the umbilicus when a surgical procedure requiring use of robust tips 20 has been completed.

Each tip dispenser 50 can also be urged through its associated opening 72 into its deployed position by a torque spring 74, as indicated in FIG. 1, that is mounted to a hinge pin associated with that tip dispenser, said torque spring unloading when an opening 72 aligns with a tip dispenser 50 as aforesaid.

Tip dispenser 50 may be formed integrally with large diameter sheath 14 by stamping or molding the structure of FIGS. 7A-C as a single piece. The hinged connection between each tip dispenser 50 and large diameter sheath 14 would then be a living hinge having an inherent bias that deploys the tip dispenser. In such embodiment, each living hinge is formed of a flexible and resilient material with memory so that each tip dispenser 50 is urged by the inherent bias of its living hinge to deploy when an opening 72 enters into registration with it. The use of a living hinge supplants the torsion or other spring.

Novel sheath 68 having handle 55 enables a user to deploy and retract tip dispensers 50 with a simple motion of two fingers placed in space 55a as best understood in connection with FIGS. 10 and 12. Handle 12a in FIG. 12 is an alternate handle for large diameter sheath 14. Handle 55a in FIG. 10 is simpler than handle 54 in FIGS. 8 and 9 because this second sheath embodiment includes no elongate rod 60.

Depending upon whether each tip dispenser 50 is hinged at its leading or trailing end, proximal-to-distal or opposite direction displacement of second sheath 68 causes openings 72 to align with tip dispensers 50 causing each of said tip dispensers to pivot under the influence of their associated bias members into said predetermined oblique angle and distal-to-proximal displacement or opposite direction displacement of said second sheath causes each of said tip dispensers to return to their respective undeployed positions.

FIGS. 10-12 also indicate that tip dispensers 50 need not be in axial alignment with one another as in the first embodiment. Handle 12a in FIG. 12 may be supplanted by handle 12 of a prior art handle.

Figure 13:
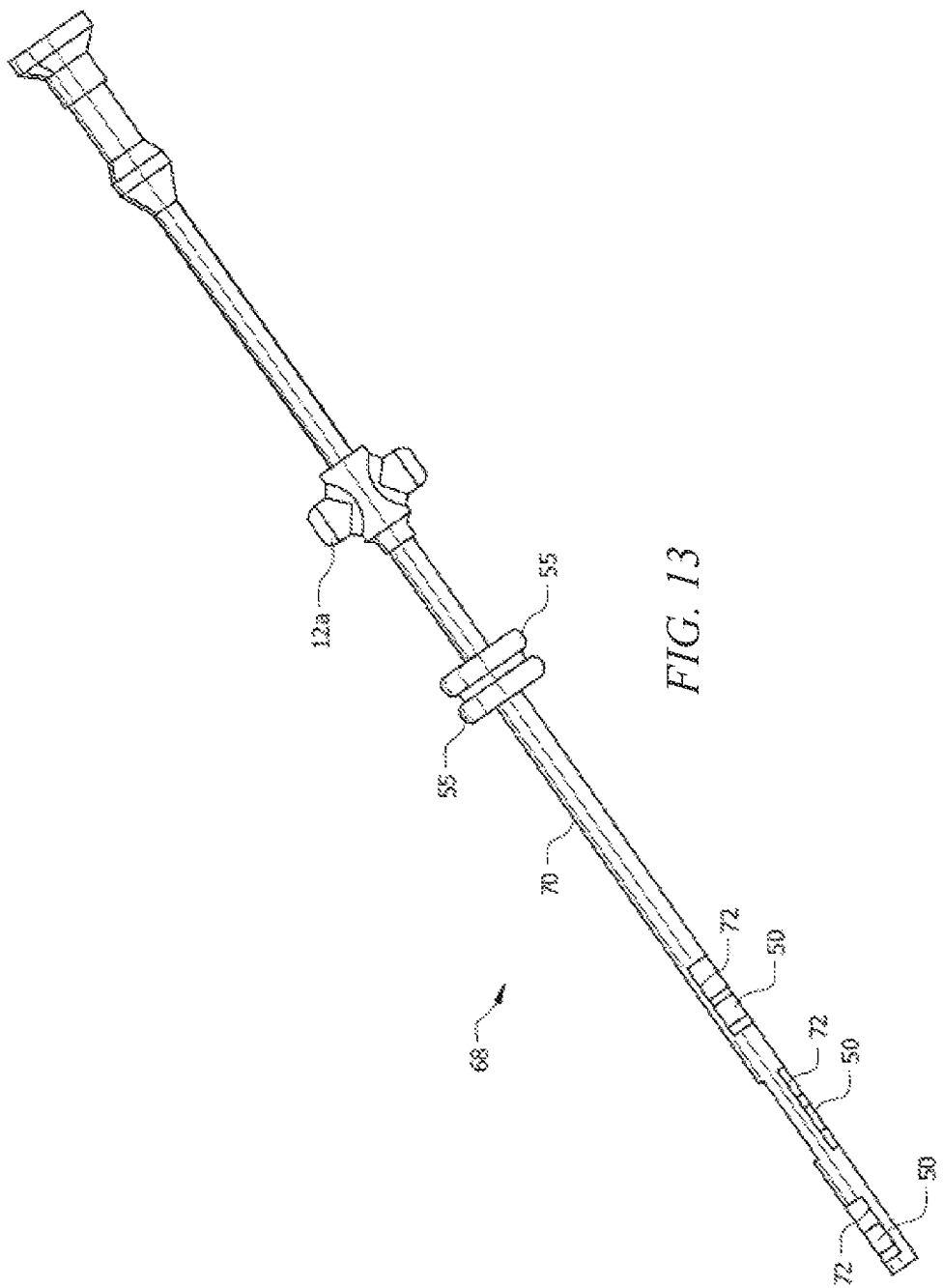
FIG. 13 is a side elevational view depicting the parts of the second embodiment and a laparoscope in their assembled configuration.

FIG. 13 is a side elevational view depicting the parts of the second embodiment and a laparoscope in their assembled configuration.

FIG. 14 is an exploded perspective view of the parts depicted in FIG. 13.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A laparoscopy tool, comprising:
a small diameter sheath having a lumen;
a control wire slideably disposed within said lumen;
a handle having a fixed position part engaged to said small diameter sheath and a movable part engaged to a proximal end of said control wire for axially displacing said control wire within said lumen in either axial direction;
a tip having opposed jaws that open and close as said control wire is displaced within said lumen,
said small diameter sheath and control wire being releasably connected to said tip;
a bore formed in a tubular trailing end of said tip;
a first and a second blade, formed of a flexible and resilient material, mounted within said bore in diametrically opposed relation to one another and extending radially inwardly towards a longitudinal axis of symmetry of said bore, said first and second blades having a common length and having radially innermost ends that are spaced apart from one another by a space having less breadth than said control wire so that said radially innermost ends of said blades are momentarily displaced in a proximal-to-distal direction when said control wire is inserted into said bore; and
a first groove formed in a leading end of said control wire on a first side thereof and a second groove formed in said leading end of said control wire on a second side thereof, said first and second grooves being transversely disposed relative to a longitudinal axis of said control wire and said first and second grooves respectively receiving said first and second blades when said control wire is inserted into said bore, said first and second blades snapping into said first and second grooves, respectively, under their inherent bias after said momentary displacement.

2. The tool of claim 1, further comprising:
said small diameter sheath having an external diameter of about 1.6 mm or less, and
said tip having a breadth greater than 1.6 mm.

3. The laparoscopy tool of claim 2, further comprising:
a third and a fourth blade, formed of a flexible and resilient material, mounted within said bore in longitudinally spaced relation to said first and second blades and in diametrically opposed relation to one another and extending radially inwardly towards a longitudinal axis of symmetry of said bore, said third and fourth blades having a common length and having radially innermost ends that are spaced apart from one another by a space having less breadth than said small diameter sheath; and
said third and fourth blades being disposed in said bore in proximal relation to said first and second blades.

4. The laparoscopy tool of claim 3, further comprising:
a earn positioned in a proximal end of said bore adjacent to said third and fourth blades, said can being centrally apertured to enable said control wire and said small diameter sheath to extend therethrough;
said cam having rises formed therein so that rotation of said cam in a first direction displaces said third and fourth blades in a proximal-to-distal direction, creating a clearance space between radially innermost ends of said third and fourth blades and said small diameter sheath so that said small diameter sheath and control wire may be introduced in a proximal-to-distal direction into the bore of said tip or withdrawn from said bore in a distal-to-proximal direction when said clearance space is created by said rotation; and
rotation of said cam in a second direction opposite to said first direction displacing said third and fourth blades in a distal-to-proximal direction, eliminating said clearance space so that radially innermost ends of said third and fourth blades engage said small diameter sheath to prevent retraction of said small diameter sheath.

5. The tool of claim 4, further comprising:
indentations formed in said rises of said cam to hold said third and fourth blades in their open position when said small diameter sheath is being introduced into or retracted from said bore.

6. The tool of claim 1, further comprising:
said tip configured to be positioned at a surgical site by a laparoscope having a large diameter sheath through an incision formed in the umbilicus of a patient, said large diameter sheath having an external diameter that exceeds 1.6 mm,
a tip dispenser in the ton of a truncate tube for housing said tip when said opposed jaws of said tip are in a closed configuration;
said tip dispenser being hingedly mounted to said large diameter sheath near the distal end of said large diameter sheath;
a cut-out irmed in said large diameter sheath that matches the length and diameter of said tip dispenser so that the outer wall of said tip dispenser is flush with the outer wall of said large diameter sheath when said tip dispenser is in an undeployed configuration;
whereby said large diameter sheath and said tip dispenser are configured to be inserted through an incision in the umbilicus, said incision being greater than 1.6 mm in extent.

7. The tool of claim 6, further comprising:
a deployment mechanism causing said tip dispenser to pivot about an axis so that a longitudinal axis of said tip dispenser is disposed at a predetermined oblique angle relative to a longitudinal axis of said large diameter sheath.

8. The tool of claim 7, further comprising:
said tip being engaged by said small diameter sheath and retracted from said tip dispenser for use in surgical procedures and said tip being returned to said tip dispenser upon completion of said surgical procedures and disengaged from said small diameter sheath.

9. The tool of claim 8, further comprising:
said deployment mechanism including an elongate rod disposed within said large diameter sheath in parallel relation to a longitudinal axis of said large diameter sheath;
a knob slideably mounted to a proximal end of said large diameter sheath;
a proximal end of said elongate rod secured to said knob so that axial displacement of said knob relative to said large diameter sheath causes conjoint axial displacement of said elongate rod;
said elongate rod being connected to said tip dispenser so that proximal-to-distal displacement of said knob causes said tip dispensers to pivot into said predetermined oblique angle and so that distal-to-proximal displacement of said knob causes said tip dispenser to return to its respective undeployed positions.

10. The tool of claim 8, further comprising:
said deployment mechanism including a second sheath that ensleeves said large diameter sheath;
said second sheath having at least one opening formed therein that is sized to allow said tip dispenser to extend through said opening when said opening is in registration with said tip dispenser;
a bias means associated with said tip dispenser that urges said tip dispenser into its deployed position;
said bias means being in a loaded configuration when said at least one opening is not in registration with said tip dispenser;
said bias means being in an unloaded configuration when said at least one opening is in registration with said tip dispenser.

* * * * *